United States Patent
Anderson et al.

(10) Patent No.: US 6,704,106 B2
(45) Date of Patent: Mar. 9, 2004

(54) METHOD AND SYSTEM FOR CANCELING SYSTEM RETARDANCE ERROR IN AN OPHTHALMOLOGICAL POLARIMETER

(75) Inventors: Michael Anderson, Lyons, CO (US); Qienyuan Zhou, Del Mar, CA (US); William Papworth, San Diego, CA (US)

(73) Assignee: Laser Diagnostic Technologies, Inc., San Diego, CA (US)

(*) Notice: Subject to any disclaimer, the term of this patent is extended or adjusted under 35 U.S.C. 154(b) by 43 days.

(21) Appl. No.: 10/160,808

(22) Filed: May 31, 2002

(65) Prior Publication Data

US 2003/0223064 A1 Dec. 4, 2003

(51) Int. Cl.[7] .................................................. G01J 4/00
(52) U.S. Cl. ........................................ 356/367; 351/215
(58) Field of Search ................................. 356/364–367; 351/215, 205–206, 221; 600/318–321, 473, 476, 558

(56) References Cited

U.S. PATENT DOCUMENTS

| | | | |
|---|---|---|---|
| 4,838,683 A | * 6/1989 | Ichihashi et al. ............ 351/221 |
| 5,209,231 A | * 5/1993 | Cote et al. ................... 600/310 |
| 5,787,890 A | * 8/1998 | Reiter et al. ................. 600/476 |
| 6,027,216 A | * 2/2000 | Guyton et al. .............. 351/200 |
| 6,112,114 A | * 8/2000 | Dreher ......................... 600/476 |
| 6,356,036 B1 | 3/2002 | Zhou ........................... 315/215 |

* cited by examiner

Primary Examiner—Hoa Q. Pham
(74) Attorney, Agent, or Firm—Michael H. Jester

(57) ABSTRACT

A polarimeter system that averages multiple retardance measurement samples to cancel the effects of system birefringence in the diagnostic path. The retardance measurement errors arising from system birefringence have a symmetry that repeats over each complete cycle of optical signal rotation cycle. This symmetry is such that averaging the four retardance measurements collected over one complete rotation cycle cancels the effects of system birefringence, leaving a mean retardance measurement free of residual polarization bias. Apparatus is provided for determining the birefringence, thickness, and fiber orientation of the nerve fiber layer at the fundus of the eye by measuring the polarization bias induced in a return beam of polarized light that is reflected at the ocular fundus from an incident beam of a known polarization state. A corneal polarization compensator cancels the birefringent effects of the cornea and other portions of the eye anterior to the fundus.

20 Claims, 9 Drawing Sheets

METHOD AND SYSTEM FOR CANCELING SYSTEM RETARDANCE ERROR IN AN OPHTHALMOLOGICAL POLARIMETER

BACKGROUND OF THE INVENTION

1. Field of the Invention

This invention relates generally to polarimeter systems for measuring polarization properties of light and more particularly to an ophthalmological system for measuring the birefringence of structural elements in the eye.

2. Description of the Related Art

The polarimeter is well-known in the optical arts and is reviewed here briefly to establish some of the terminology required for this disclosure. A single-beam polarimeter measurement usually consists of an optical signal in a single state of polarization. Some form of "analyzer" within the polarimeter removes all but a single state of polarization from the incoming light, which is then measured and recorded with a suitable detector as a charge-coupled device (CCD). A series of measurements is usually made with a different state of polarization being recorded for each. These measurements allow both the degree and orientation of the optical signal polarization to be estimated and recorded. The single rotatable analyzer passes only light polarized parallel to a specified axis so the analyzer must be rotated about the optical beam axis to measure light polarized in different directions. A single fixed analyzer passes light polarized parallel to its axis and cannot be rotated but a polarization rotator such as, for example, a half-wave plate, may be placed in the optical beam axis to rotate the plane of polarization of the incoming optical signal before it reaches the fixed analyzer. Light polarized in different directions can thus be measured by rotating the half-wave plate.

A half-wave plate has a preferred ("fast") axis. Light polarized parallel to this axis passes through the half-wave plate unchanged. Light polarized perpendicular to the fast axis (parallel to the "slow" axis) is retarded by half a wavelength. The net effect of this is to rotate the plane of polarization of the light so that the axis of the half-wave plate bisects the angle between the planes of polarization in the incoming and outgoing light. Using similar reasoning, it may be shown that the net effect of a precise one-quarter wavelength retardance is to bias the linear polarization components of the entering light into equivalent circular polarization components, as is well-known in the art.

The single beam polarimeter is exemplified by the polarimeter 20 shown functionally in FIG. 1. The optical signal 22 arrives along the optical beam axis 24 and the half-wave plate 26 rotates the original polarization angle 22 to a new angle 28 by means of the position of its fast axis 30. The fixed analyzer 32 then blocks all of optical signal 28 except for the particular component 32 parallel to the analyzer axis 36, which is then received by the detector 38. Detector 38 may then generate an electrical signal 40 representative of the intensity of the optical signal 34. FIG. 2 shows a reference direction 42 aligned with analyzer axis 36 of fixed analyzer 32 within an arbitrary focal plane at detector 38. The orientation of rotating half-wave plate 26 is specified by the difference angle 44 between reference direction 42 and half-wave plate axis 30. The combination of fixed analyzer 32 and rotating half-wave plate 26 can be thought of as equivalent to a single rotating analyzer that rotates twice as fast as half-wave plate 26. As shown in FIG. 2, the anticlockwise angle 44 from reference direction 42 to half-wave plate axis 30 is doubled to give the effective analyzer position 46. Thus, by rotating half-wave plate 26 over a 180-degree range, the effective analyzer position 46 is rotated over a complete 360-degree cycle.

References to birefringence herein refer to intrinsic birefringence or form birefringence, a property of a material that causes a change in the polarization of light which passes through it. Birefringence has two components; orientation (or axis) and magnitude. Form birefringence is found in materials consisting of a substantially parallel array of many small cylindrical structures that are small with respect to the wavelength of the light passing through it. Such form birefringence is a measurable property of the retinal nerve fiber layer (RNFL) that is useful for determining RNFL thickness. Form birefringence is also a measurable property of the Henle fiber layer that is similarly usefull for determining Henle fiber layer thickness.

Knowing the thickness of a patient's RNFL can be crucial in diagnosing glaucoma and other optic nerve diseases. The RNFL birefringence introduces retardance into any polarized beam of light passing through the RNFL when the beam polarization axis is neither parallel nor perpendicular to the nerve fiber bundles making up the RNFL. Birefringence is an optical property associated with the anisotropy of a medium through which polarized light propagates, and is manifested by the retardance of some components of the light resulting from variation of light velocity in the medium with propagation direction and polarization axis. When light propagates perpendicularly to the optic axis of an anisotropic material, the two orthogonally-polarized (S and P) components of the light, one with polarization parallel to the fast axis and the other with polarization perpendicular to the fast axis (parallel with the "slow" axis), travel through the material at different velocities, introducing a phase shift between the two components. This phase shift is known in the art as retardation or retardance and is herein denominated "retardance."

A beam of light entering a patient's eye encounters the retina and scatters back from it. The polarization state of the emerging directly-backscattered light changes based on the amount of retardance between the two S and P components. A retardance map can be generated based on the backscattered light that represents the thickness of the RNFL and, hence, that is useful for diagnosing maladies of the eye.

Accordingly, the commonly-assigned U.S. Pat. Nos. 5,303,709, 5,787,890, 6,112,114, and 6,137,585, entirely incorporated herein by reference, disclose laser diagnostic devices that measure the thickness of the RNFL by measuring the amount of retardance of laser light in the RNFL layer, with the amount of retardance then being correlated to RNFL thickness in accordance with principles known in the art. Likewise, the so-called Henle fiber layer, which includes photoreceptor axons and which has radially distributed slow axes centered about the fovea in the macula of the eye, is also form birefringent and consequently, its thickness also can be measured for diagnostic purposes using laser light.

However, portions of the eye (hereinafter collectively denominated "anterior segments") that are anterior to the retinal nerve and Henle fiber layers may also be birefringent. For example, both the cornea and lens are birefringent. Moreover, the axial orientation and magnitude of birefringence of the anterior segments may vary significantly from person to person. Because a diagnostic beam must pass through these anterior segments, the laser beam retardance caused thereby must be accounted for, to isolate the retardance of posterior segments such as the retinal nerve fiber and Henle fiber layers. When measuring RNFL birefringence from the front of the eye, a compensating device is needed to remove the retardance contribution of the anterior segments from the birefringence measurement.

The above-mentioned U.S. Pat. No. 5,303,709 disclosed a corneal compensator for neutralizing the effects of the birefringence of anterior segments of the eye on a diagnostic beam meant to measure the thickness of the RNFL. The compensating structure of the '709 patent includes a polarization-sensitive confocal system attached to a scanning laser retinal polarimeter. The detector of this apparatus includes a pinhole aperture set to be conjugate with the laser source and the posterior surface of the crystalline lens so that only reflected light from the posterior surfaces of the crystalline lens is captured and analyzed. A variable retarder is then set to null any retardance in the returned light beam, which represents a measurement of anterior segment retardance.

The above-cited ophthalmological systems send laser light traveling through the retinal nerve and Henle fiber layer structures and back, reflecting off the retinal pigment epithelium or inner retina. The light assumes a retardance (polarization bias) proportional to the amount of parallel birefringent structures (microtubules) traversed.

The commonly-assigned U.S. Pat. No. 6,356,036 B1, entirely incorporated herein by reference, discloses yet another method and apparatus for measuring the magnitude and axial orientation of birefringence in both the anterior and the posterior segments of the human eye. The anterior segment includes essentially the combined birefringence of the cornea and the crystalline lens, and the posterior segment includes regions at the fundus. The optical axis and the magnitude of the birefringence of the anterior segment is first determined, then the birefringence of the posterior segment is canceled by a variable retarder. The measured birefringence of the cornea, lens and other segments of the eye anterior to the retina are used to perform certain post-measurement calculations to provide accurate anterior segment compensation despite eye movement. The birefringence of the posterior segment is then determined without interference of the birefringence of the anterior segment. The apparatus and method are applicable to the measurement of the birefringence of the retinal nerve fiber layer at the peripapillary region and the birefringence of the Henle fiber layer at the macular region of the retina. The described a procedure uses the patient's Henle fiber layer (instead of the lens posterior surface) as a reference surface for determining anterior segment birefringence. In principle, any useful reflecting surface in the eye can be used with the disclosed method as long as the surface may be characterized to eliminate its effects on the reflected signals.

The measuring apparatus described in the above-cited patents includes, for example, variable retarders, polarizing beam splitters and rotatable half-wave and quarter-wave retarders ("wave-plates"). A half-wave plate is one example of a fixed retarder or polarization rotator, which has a preferred or "fast" axis. Light that is linearly polarized in alignment with the fast axis passes through the fixed retarder unchanged. Light that is linearly polarized orthogonally to the fast axis is aligned with the "slow" axis of the retarder and is retarded in phase by an amount representing the "retardance" of the fixed retarder. This is, for example, one-half wavelength for a half-wave retarder, one-quarter wavelength for a quarter-wave retarder, and so forth.

As is well-known in the art, a general polarimeter may be used to measure the polarization properties, such as, for example, the Stokes Vector [I, Q, U, V], of any optical signal. The Stokes parameters form a four-component vector that completely characterizes the polarization characteristics of an optical signal. The various components of the Stokes vector may be characterized as simple combinations of intensity outputs from various combinations of linear or circular polarizers, where I is the total optical signal intensity, Q is the intensity difference between the horizontal and vertical linearly-polarized optical signal components, U is the intensity difference between the linearly-polarized optical signal components oriented at ±45 degrees, and V is the intensity difference between the right and left circularly-polarized optical signal components.

Disadvantageously, the retardance of a "half-wave retarder" is precisely equal to one-half wavelength only at a single, optical frequency. As is well-known in the art, the accuracy of polarimetry measurements depend in part on the precision of such optical components, which may be precisely matched to a single optical wavelength, $\lambda_0$. For example, when used with light having a different wavelength, $\lambda$, a half-wave retarder introduces a $\lambda/2\lambda_0$ delay instead of a half-wave delay into the signal. Similarly, a quarter-wave retarder introduces a $\lambda/2\lambda_0$ delay instead of a quarter-wave delay. While the optical frequency can be controlled very precisely, a mere 2.5 nanometer fabrication error in a half-wave retarder results in a retardance error varying from nothing to more than one degree, depending on the orientation axis of the birefringent structure being measured. Moreover, each of the optical system elements may introduce similar biasing errors, contributing to a residual system birefringence in the diagnostic optical path, which may contribute to a significant measurement error.

This is a significant problem when using the above-described polarimetry techniques to map the birefringence of the retinal nerve or Henle fiber layers in the eye because these layers have birefringence orientation axes at all angles. The system birefringence (which herein is defined to include polarization rotator retardance error) of the optical components introduces retardance measurement errors that vary unevenly over a typical RNFL or Henle fiber layer thickness map, unpredictably distorting the desired medical analysis. To keep these errors acceptably small, the (residual) system retardance over the entire diagnostic beam path must be held under two degrees. This increases the precision and care needed during the manufacture and assembly of a commercial ophthalmological apparatus for mapping the RNFL birefringence in the eye, thereby disadvantageously increasing cost and reducing measurement reliability.

There is accordingly a clearly-felt need in the art for a method that eliminates system birefringence error in the diagnostic path of a polarimeter, which would improve manufacturability and measurement reliability by relaxing tolerances during manufacture, thereby permitting the use of a wider range of components while maintaining system accuracy. The resulting improvement in polarimeter accuracy would also improve the accuracy of the above-described techniques for anterior segment retardance compensation in an ophthalmological polarimeter, thereby improving ophthalmological structure mapping accuracy. The related unresolved problems and deficiencies are clearly felt in the art and are solved by this invention in the manner described below.

SUMMARY OF THE INVENTION

This invention solves the above-described system birefringence problems by, for the first time, introducing a method for averaging multiple retardance measurement samples to cancel the effects of system birefringence in the diagnostic path. This invention results in part from the unexpectedly advantageous observation that the retardance measurement errors arising from system birefringence have a symmetry that repeats over each complete rotation cycle of optical signal polarization when effected with any useful polarization rotator, such as, for example, a half-wave retarder. Because the optical signal polarization angle rotation is doubled by the physical rotation of a half-wave retarder, the system birefringence errors repeat with every half-cycle (180 degrees) of half-wave retarder rotation. The character of this error symmetry is such that averaging the four retardance measurements collected over one such rotation cycle cancels the effects of system birefringence, leaving a mean retardance measurement free of such errors.

It is a purpose of this invention to provide an ophthalmological system and method for measuring the birefringence of structural elements in the eye with improved accuracy and eased manufacturing tolerances.

It is an advantage of this invention that combining four retardance samples over a single polarization rotation cycle cancels errors arising from system birefringence in the optical path and from any polarization rotator mismatch with the optical signal frequency, thereby reducing requisite manufacturing tolerances for the important system optical components, such as, for example, the beam splitters, lenses, scanners and retarders.

It is another advantage of this invention that the same sampling and averaging technique substantially improves accuracy and manufacturability in a general polarimeter system for measuring the polarization of any analyzed optical signal.

In one aspect, the invention is a method for analyzing a structure in the interior of an eye having a pupil, including the steps of (a) producing an optical diagnostic signal having a predetermined polarization state, (b) directing the optical diagnostic signal into the eye through the pupil, such that the optical diagnostic signal is reflected from the structure back through the pupil, (c) producing an electrical signal having a magnitude S representing the polarization state of the reflected optical diagnostic signal as biased by a system birefringence, (d) rotating the reflected optical diagnostic signal polarization about an optical beam axis over a substantially ninety (90) degree range within which the electrical signal magnitude S varies between two extrema [$S_{max}$, $S_{min}$], (e) averaging a plurality of electrical signal magnitude extrema {$S_{max}$, $S_{min}$} obtained during rotation of the reflected optical diagnostic signal polarization over a substantially three-hundred-and-sixty (360) degree range to produce one or more mean electrical signal magnitude extrema signals [$\overline{S}_{max}, \overline{S}_{min}$] representing the polarization state of the reflected optical diagnostic signal unbiased by the system birefringence, and (f) producing, responsive to the mean electrical signal magnitude extrema signals [$\overline{S}_{max}, \overline{S}_{min}$], an analysis signal representative of a property of the structure.

In another embodiment, the invention is an apparatus for analyzing a structure in the interior of an eye having a pupil, including an optical source for producing an optical diagnostic signal having a predetermined polarization state, an optics system coupled to the optical source for directing the optical diagnostic signal into the eye through the pupil, such that the optical diagnostic signal is reflected from the structure back through the pupil to the optics system, an optical polarization detector for producing an electrical signal having a magnitude S representing the polarization state of the reflected optical diagnostic signal as biased by a system birefringence, a polarization rotator for rotating the reflected optical diagnostic signal polarization about an optical beam axis over a substantially ninety (90) degree range within which the electrical signal magnitude S varies between two extrema [$S_{max}$, $S_{min}$], a processor coupled to the optical polarization detector for producing, responsive to the polarization state of the reflected optical diagnostic signal, an image signal representative of a property of the structure, and an averager for averaging a plurality of electrical signal magnitude extrema {$S_{max}$, $S_{min}$} obtained during rotation of the reflected optical diagnostic signal polarization over a substantially three-hundred-and-sixty (360) degree range to produce one or more mean electrical signal magnitude extrema signals [$\overline{S}_{max}, \overline{S}_{min}$], representing the polarization state of the reflected optical diagnostic signal unbiased by the system birefringence.

In yet another aspect, the invention is a method for measuring the unbiased polarization state of an analyzed optical signal in an optical polarimeter system including the steps of (a) producing an electrical signal having a magnitude S representing the polarization state of the analyzed optical signal as biased by the system birefringence, (b) rotating the analyzed optical signal polarization about an optical beam axis over a substantially ninety (90) degree range within which the electrical signal magnitude S varies between two extrema [$S_{max}$, $S_{min}$], and (c) averaging a plurality of electrical signal magnitude extrema {$S_{max}$, $S_{min}$} obtained during rotation of the analyzed optical signal polarization over a substantially three-hundred-and-sixty (360) degree range to produce one or more mean electrical signal magnitude extrema signals [$\overline{S}_{max}, \overline{S}_{min}$] representing the polarization state of the analyzed optical signal unbiased by the system birefringence.

In yet another embodiment, the invention is an optical polarimeter system for measuring the polarization state of an analyzed optical signal including an input for accepting the analyzed optical signal, an optical polarization detector for producing an electrical signal having a magnitude S representing the polarization state of the analyzed optical signal as biased by a system birefringence, a polarization rotator for rotating the analyzed optical signal polarization about an optical beam axis over a substantially ninety (90) degree range within which the electrical signal magnitude S varies between two extrema [$S_{max}$, $S_{min}$], and a processor coupled to the optical polarization detector for averaging a plurality of electrical signal magnitude extrema {$S_{max}$, $S_{min}$} obtained during rotation of the analyzed optical signal polarization over a substantially three-hundred-and-sixty (360) degree range to produce one or more mean electrical signal magnitude extrema signals [$\overline{S}_{max}, \overline{S}_{min}$] representing the polarization state of the analyzed optical signal unbiased by the system birefringence.

The foregoing, together with other objects, features and advantages of this invention, can be better appreciated. with reference to the following specification, claims and the accompanying drawing.

BRIEF DESCRIPTION OF THE DRAWINGS

For a more complete understanding of this invention, reference is now made to the following detailed description of the embodiments as illustrated in the accompanying drawing, in which like reference designations represent like features throughout the several views and wherein.

DESCRIPTION OF THE PREFERRED EMBODIMENT

As used herein, the term polarization "biasing" generically covers all types of polarization changes, including the rotation of the optical axis of polarized light, the change of linear to elliptically or circularly polarized light or vice-versa, and any combination of these. The term "polarimetry" refers to techniques for determining the polarization "bias" of a light beam. The term "polarimeter" refers to devices for performing polarimetry. The terms "spatially resolved retinal polarimery" and "spatially resolved retinal polarimeter", refer to the technique and device for performing polarimetry, point by point, on the retina. The term "retardance map" refers to a two-dimensional display of retardance distribution measured with a spatially resolved polarimeter. The term "corneal birefringence" means anterior segment birefringence, including contributions of the lens in addition to the cornea; and the term "corneal compensator" is used to describe a device for neutralizing the birefringence of the anterior segment of the eye, such as a variable retarder.

Figure 3:
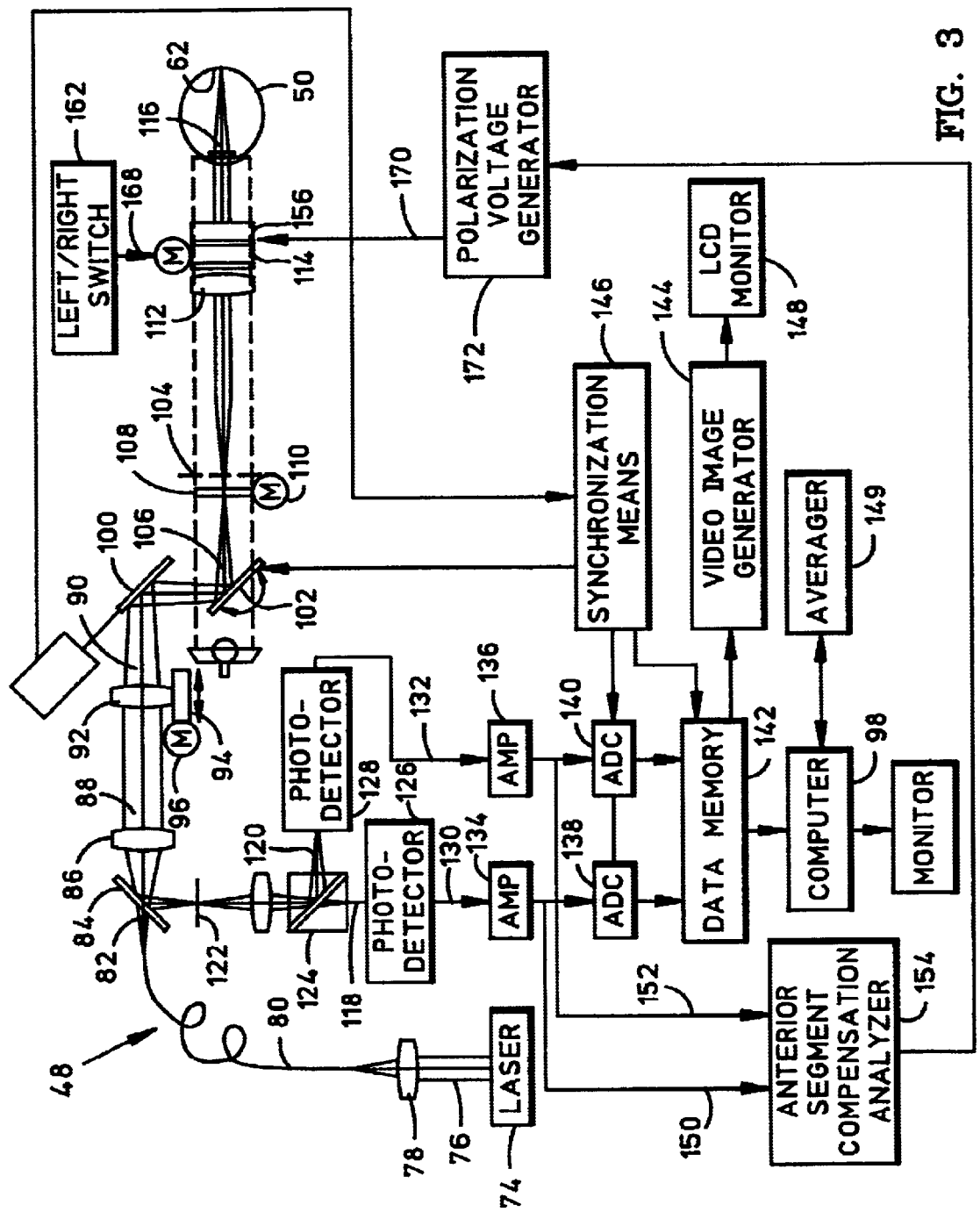
FIG. 3 is a block diagram illustrating an exemplary embodiment of the opthalmological apparatus of this invention.
Figure 3B:
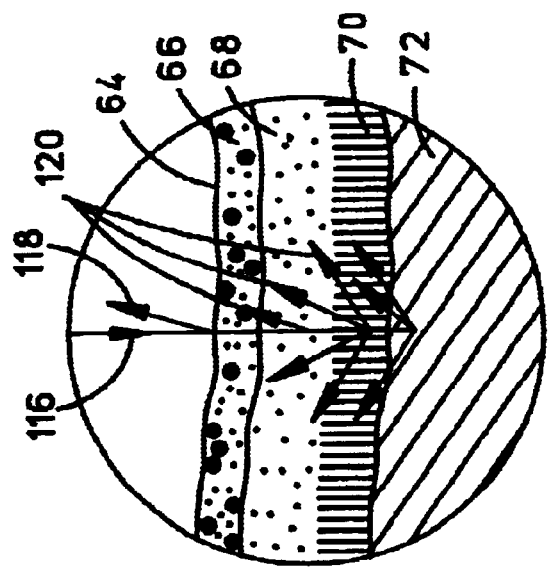
FIGS. 3A and 3B illustrate the elements of the eye related to the opthalmological apparatus for use in the opthalmological apparatus of this invention.
Figure 3A:
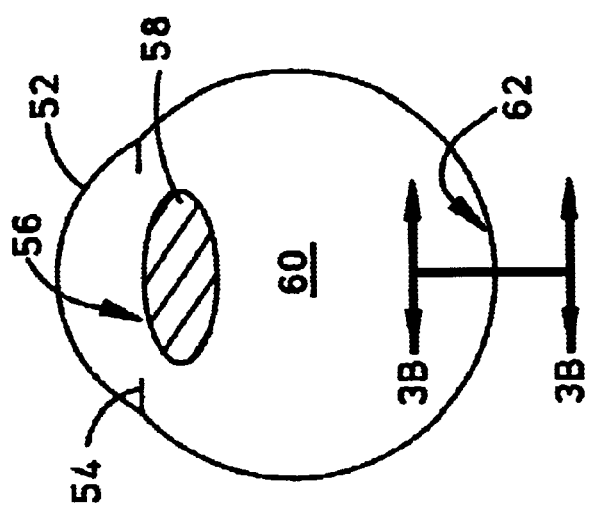

FIG. 3 is a block diagram illustrating the opthalmological apparatus 48 of this invention for analyzing the eye 50, which is described in FIGS. 3A and 3B. Eye 50 includes the cornea 52 as the foremost, transparent portion of eye 50, behind which is the iris 54 (having a pupil 56) and the lens 58. The interior 60 of eye 50 is filled with vitreous humor. The back of eye 50 includes the retina (FIG. 3B), composed of many layers or structures, including, in the area of the fundus 62, the internal limiting membrane 64, the retinal nerve fiber layer (RNFL) 66, the receptor system 68, the retinal pigment epithelium 70, the choroid 72 and the Henle fiber layer (not shown), which is generally located at the level of RNFL 66. AD structures forward of membrane 64 are considered part of the anterior segments of eye 50 for purposes of this disclosure.

Apparatus 48 is suitable for analyzing a structure in eye 50 to provide, for example, an image map of the thickness of RNFL 66 or the Henle fiber layer (not shown). In accordance with this invention, a polarized diode laser 74 of wavelength 780 nm provides a source of the optical diagnostic signal 76. Although light of any wavelength that passes the ocular media may be used, a diode laser wavelength 780 nm is an excellent compromise between optical performance, patient comfort, and laser safety. Linearly-polarized optical diagnostic signal 76 is focused by the coupling lens 78 onto a polarization-maintaining, single-mode optical fiber 80. The diverging optical signal beam 82 emerging from optical fiber 80 impinges upon the beam splitter 84, which may be a polarizing beam splitter, a non-polarizing beam splitter or a partially polarizing beam splitter. In one embodiment, beam splitter 84 reflects roughly 99% of any optical signal polarized perpendicular to the plane of incidence and transmits about 85% of any optical signal polarized parallel to the plane of incidence. Because diverging optical beam 82 is substantially polarized parallel to the plane of incidence, about 85% of the signal impinging upon beam splitter 84 is transmitted through and collected by the lens 86 to generate a collimated optical beam 88. Collimated optical beam 88 is converged to a converging optical beam 90 by the focusing lens 92, which is mounted on a focus translation stage 94. A stepper motor 96 is used to move lens 92 under control of, for example, a computer 98.

Consequently, converging optical beam 90 is deflected by the resonant scanner 100 to scan in the horizontal direction at a frequency of about 4500 Hz and the galvanometer scanner 102 in the vertical direction at a frequency of about 30 Hz, generating a focused two-dimensional laser raster 104. At each point of the scan, in accordance with this invention, the scanned laser optical signal 106 penetrates a polarization rotator consisting of a half-wave plate 108 and the stepper motor-controlled drive mechanism 110. Half-wave plate 108 rotates the polarization axis of scanned converging optical signal 106 without geometrically rotating focused two-dimensional laser raster 104.

Focused two-dimensional laser raster 104 is focused (imaged) by the lens 112 onto fundus 62 of eye 50 through a variable retarder 114, cornea 52, pupil 56 and lens 58. By moving focusing lens 92, focused raster scan pattern 104 may be imaged onto different layers of fundus 62. The illuminating optical beam 116 is specularly reflected from internal limiting membrane 64 of fundus 62, generating the specular reflection optical beam 118. The state of polarization of specular reflection optical beam 118 is substantially identical to the polarization state of illuminating optical beam 116, except for a 180-degree phase shift occurring during specular reflection. The remainder of illuminating optical beam 116 penetrates the form-birefringent RNFL 66 and is partially reflected by the more-posterior retinal layers, thereby twice-passing RNFL 66 and forming the diffuse reflection optical beam 120. Because of the form-birefringent properties of RNFL 66, the state of polarization of the diffuse reflection optical beam 120 is changed compared to the state of polarization of the illuminating optical beam 116.

Specular reflection optical beam 118 and diffuse reflection optical beam 120 exit eye 50 through lens 58, pupil 56 of iris 54, and cornea 52, and travel back along substantially the same optical path as described above until they impinge upon beam splitter 84, where they are separated from diverging optical beam 82. Lens 86 focus specular reflection optical beam 118 and diffuse reflection optical beam 120 onto the pinhole aperture 122, which is located at a plane conjugate to the exit aperture of optical fiber 80, the plane of focused two-dimensional laser raster 104, and the plane of fundus 62.

Specular reflection optical beam 118 and diffuse reflection optical beam 120 passing through pinhole aperture 122 are separated by a polarizing beam splitter 124 or a similar arrangement of polarizers and beam splitter. Polarizing beam splitter 124 transmits all light having a state of polarization identical to the state of polarization of diverging optical beam 82, thereby allowing it to be imaged onto a photodetector 126. Any light having a polarization different from the polarization of diverging optical beam 82 is reflected by beam splitter 124 and thereby imaged onto the second photodetector 128. The output signals 130 and 132 from photodetectors 126 and 128 are amplified by the amplifiers 134 and 136 and digitized by the analog-to-digital converters 138 and 140. The amplified and digitized outputs of the photodetectors 126 and 128 are then stored in a dual ported data memory 142, which is accessible by computer 98 and the video image generator 144.

A synchronizer 146 is triggered by the oscillating frequency of the resonant scanner 100 and generates the driving signal for the galvanometer scanner 102. In addition, synchronizer 146 controls the memory location address within data memory 142 so that each amplified and digitized output of each of photodetectors 126 and 128 can be correlated with the scan position of resonant scanner 100 and galvanometer scanner 102 at the time of data sampling. In one embodiment, for example, 256 data samples of each of photodetectors 126 and 128 are acquired, digitized, and stored along one horizontal scan line, and 256 scan lines at gradually changing vertical positions are acquired before the scan procedure is repeated. Video image generator 144 immediately reads the data samples from dual ported data memory 142 and generates a video image that may be displayed on a liquid crystal display device 148, for example. In accordance with this invention, in opthalmological apparatus 48, a plurality of signal samples arm collected in data memory 142 for each scan position and the extrema (maxima and minima) are selected and averaged in the averager 149 over a 180-degree range of rotation of half-wave plate 108 to obtain the mean signal extrema [$\overline{S}_{max}$, $\overline{S}_{min}$] representing the retardance of the scan position in the structure at fundus 62, unbiased by the system birefringence including the birefringence of half-wave plate 108. The rotation of half-wave plate 108 over the necessary range may proceed concurrently with the two-dimensional scan provided by resonant scanner 100 and galvanometer scanner 102, thereby providing for each scan position in raster 104 a series of samples over the 180-degree rotation of half-wave plate 108. The sample sequences (see FIG. 5 described below) for different scan positions may represent slightly different rotational positions of half-wave plate 108, but the spacing and usefulness are generally identical for every scan position. Signal extrema are determined and averaged according to this invention for each of the scan positions in raster 104.

In parallel to the data acquisition process described above, amplified output signals 150 and 152 of photodetectors 126 and 128 are analyzed by the anterior segment compensation analyzer 154. If there is no birefringence in the anterior segments of the eye, then specular reflection optical beam 118 has the same state of polarization as diverging optical beam 82, and, is thereby completely imaged onto photodetector 126. Photodetector 128 then receives only diffuse reflection optical beam 120. However, because the anterior segments of the eye are birefringent, the state of polarization of specular reflection optical beam 118 is thereby changed so an additional optical signal component is detected by photodetector 128, reducing output signal 130 from photodetector 126.

Variable retarder 114 may include, for example, a combination of a plurality of fixed optical retarders, including a layer of liquid crystal material 156 Variable retarder 114 can be rotated along its axis by a motor 158 and a drive belt 160. A proximity switch 162 located in the tabletop 164 automatically detects the position of the eye disease examination device 166 to determine if the left or right eye is being examined. The left/right eye signal 168 from proximity switch 162 is used to control the motor 158, which rotates the variable retarder 114 so that the optic axis of the variable retarder substantially coincides with the measured fast axis of the birefringence of the anterior segments (including cornea 52) of eye 50.

A varying voltage signal 170 generated by the polarization voltage generator 172 and applied to variable retarder 114 varies the polarization properties of liquid crystal layer 156 and, therefore, the amount of change in the state of polarization introduced to a optical beam passing through variable retarder 114. Other fixed or variable retarders or combinations thereof, such as, for example, a Pockets cell, a Kerr cell, a Soleil-Babinet retarder, combinations of rotating fixed retarders, and the like may be employed instead of liquid crystal layer 156 described for this exemplary embodiment.

A closed loop circuit 174 changes output 170 from polarization voltage generator 172 until output signal 130 from photodetector 126 is maximized and output signal 132 from photodetector 128 is minimized. In this state, the amount of polarization bias introduced to an optical signal when, passing through anterior polarization compensator 114 effectively cancels the polarization bias introduced to the same optical beam when passing through the anterior segments of eye 50. Once the anterior segment polarization effects are cancelled, signal outputs 130 and 132 from photodetectors 126 and 128 represent only the birefringence of the posterior retinal layers and therefore may be used to represent the topography and the thickness of RNFL 66, for example. Anterior segment birefringence compensation in this fashion is automatic, with real-time feedback, but is needed only once at the beginning of a scanning session and need not be updated for every scanned point. Although anterior segment retardance varies somewhat from point-to-point across the cornea, only one point is penetrated by the diagnostic beam in a scanning session.

Figure 1:
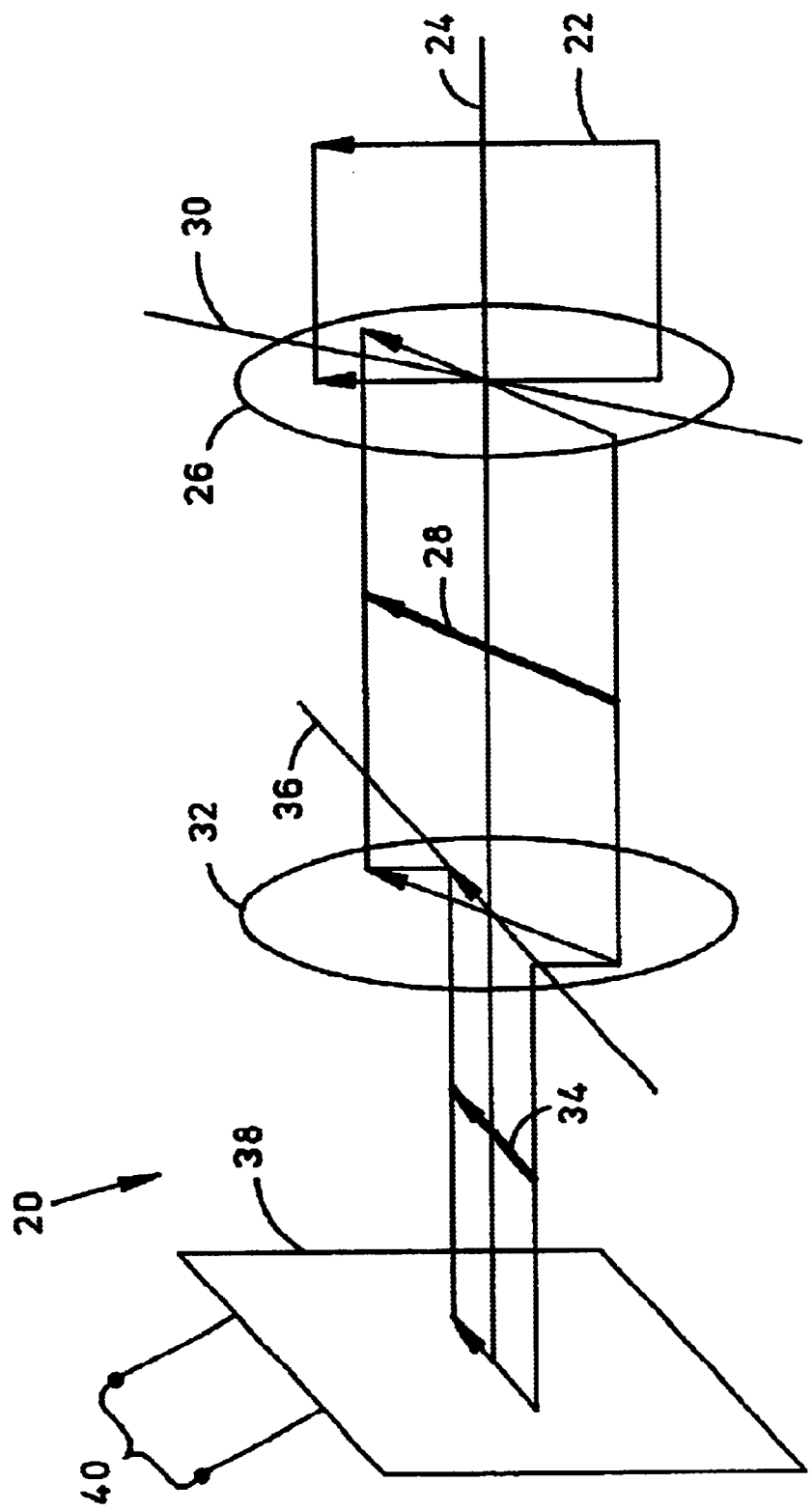
FIG. 1 is a schematic representation of a typical single-beam polarimeter from the prior art.
Figure 2:
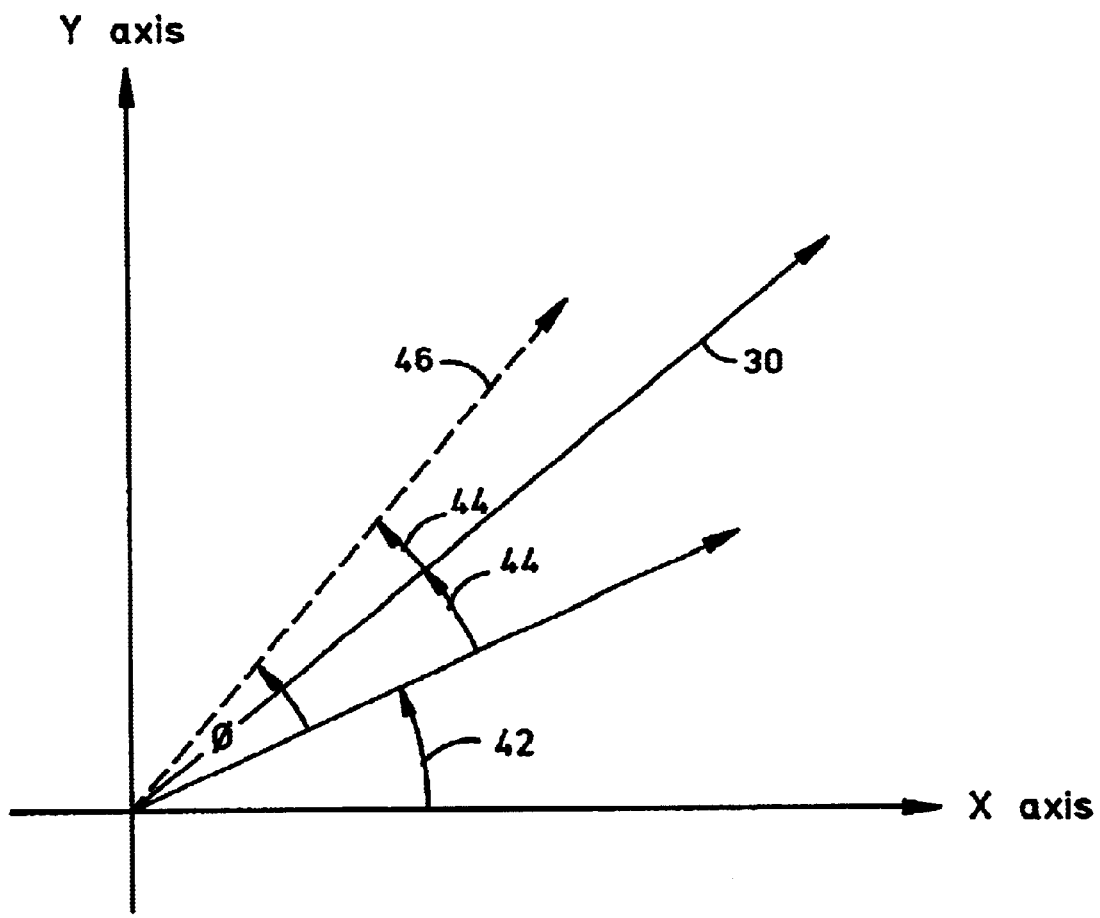
FIG. 2 is a chart illustrating the relationship among component polarization angles for the polarimeter from FIG. 1.
Figure 4:
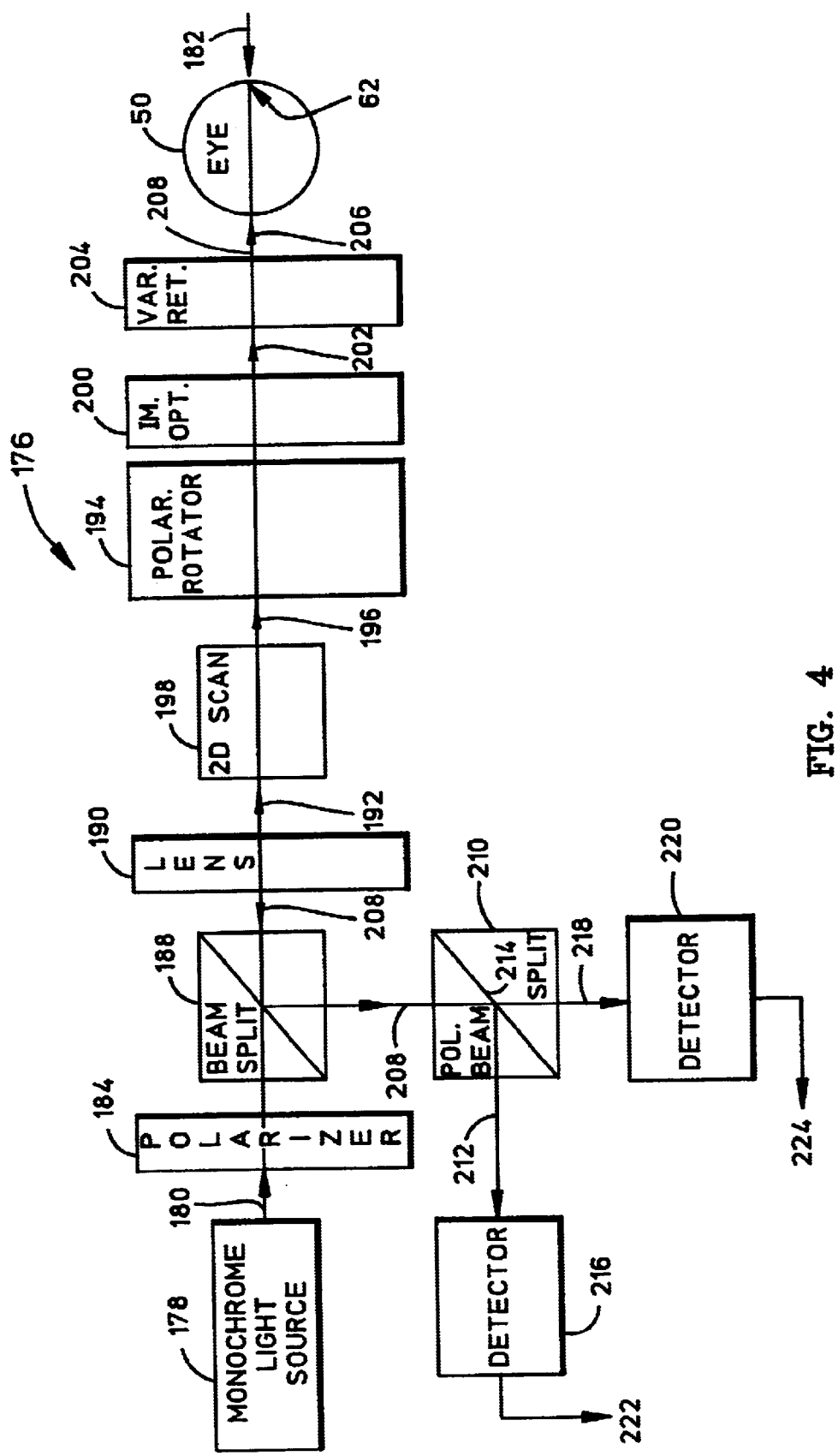
FIG. 4 is a block diagram illustrating another exemplary embodiment of a polarimeter apparatus in accordance with this invention.

FIG. 4 is a block diagram illustrating another exemplary embodiment of the polarimeter portion 176 of the opthalmological apparatus of this invention. The optical system 176 includes a monochromatic light source 178, such as a laser, generating a monochromatic diagnostic optical signal 180 propagating along a beam axis 182. Diagnostic optical signal 180 passes through a polarizer 184 to bias the polarization of diagnostic optical signal 180 to a polarization axis that is selected to be either parallel or perpendicular to the incidence plane 186 of a non-polarizing beam splitter 188. Optical signal 130 is then collimated by a lens 190 to form a collimated beam 192, which passes through a scanning unit 198 to create the scan field 196. In one embodiment, scanning unit 198 includes a two-dimensional scanning device. Any useful conventional two-dimensional scanning device may be used in scanning unit 198. In another exemplary embodiment using two one-dimensional line scanners (not shown), a first line scanner performs a line scan and a second one-dimensional scanner steps along a direction orthogonal to the first line scan upon the completion of each first line scan. Two-dimensional scan field 196 is thereby generated and is then projected through a polarization rotator 194, thereby rotating the linear polarization axis of each element of scan field 196 by an angle θ. In one embodiment, rotator 194 includes a rotatable half-wave plate such that the polarization rotation angle θ is determined by the angular relationship between the polarization of collimated beam 192 and the axis of half-wave retarder 34 in the well-known manner (see FIG. 2, for example). In another exemplary embodiment, rotator 194 may include a liquid-crystal (LC) variable retarder that can be electronically rotated to provide any desired polarization rotation angle θ within one 360-degree polarization rotation cycle. The rotated polarized scan field from rotator 194 is then passed through an imaging optics unit 200, which can include an objective lens and a focusing unit to dynamically compensate for refraction errors in the anterior segments of the eye.

From imaging optics unit 200, the scanning beam 202 next passes through a variable retarder 204. As fully described in the above-cited commonly-assigned patents, variable retarder 204 serves as a corneal compensator that is useful for measuring and canceling the retardance of the anterior segments of the eye. Variable retarder 204 may, for example, include a liquid crystal (LC) variable retarder with controlled orientation of the fast and slow axes or it may include two zero-order fixed retarders of any useful configuration, for example.

After the retarded scanned optical signal 206 encounters fundus 62 of eye 50, it is backscattered or reflected therefrom, propagating back as a reflected diagnostic optical signal 208, sharing the same beam path with diagnostic optical signal 180 through optical system 176 until it is redirected (because of the polarization bias arising from its specular reflection from fundus 62) by beam splitter 188 towards a polarizing beam splitter 210. Polarizing beam splitter 210 separates reflected optical signal 208 into two orthogonally-polarized components in the usual manner. One component 212 with a polarization axis perpendicular to the incidence plane 214 of beam splitter 210 is reflected to a first detector 216, and another component 218 with polarization axis parallel to incidence plane 214 is transmitted to a second detector 220. Detectors 216 and 220 each produce an electrical signal 222 and 224, respectively, that represents the intensities of optical signals 212 and 218. When the polarization angle is rotated about beam axis 182 by rotator 194, the magnitudes of signals 222 and 224 each vary between two (different) extrema on different schedules. Either one or both electrical signals 222 and 224 may be normalized by some suitable processor (such as, for example, computer 98 in FIG. 3) with respect to the total intensity of the two signals 212 and 218. So, for example, when signal 222 is normalized to total intensity to produce a normalized signal 226, signal 226 then varies between two extrema over the range of rotation of, for example, a half-wave plate embodiment of rotator 194 in the manner illustrated in FIG. 5.

Figure 5:
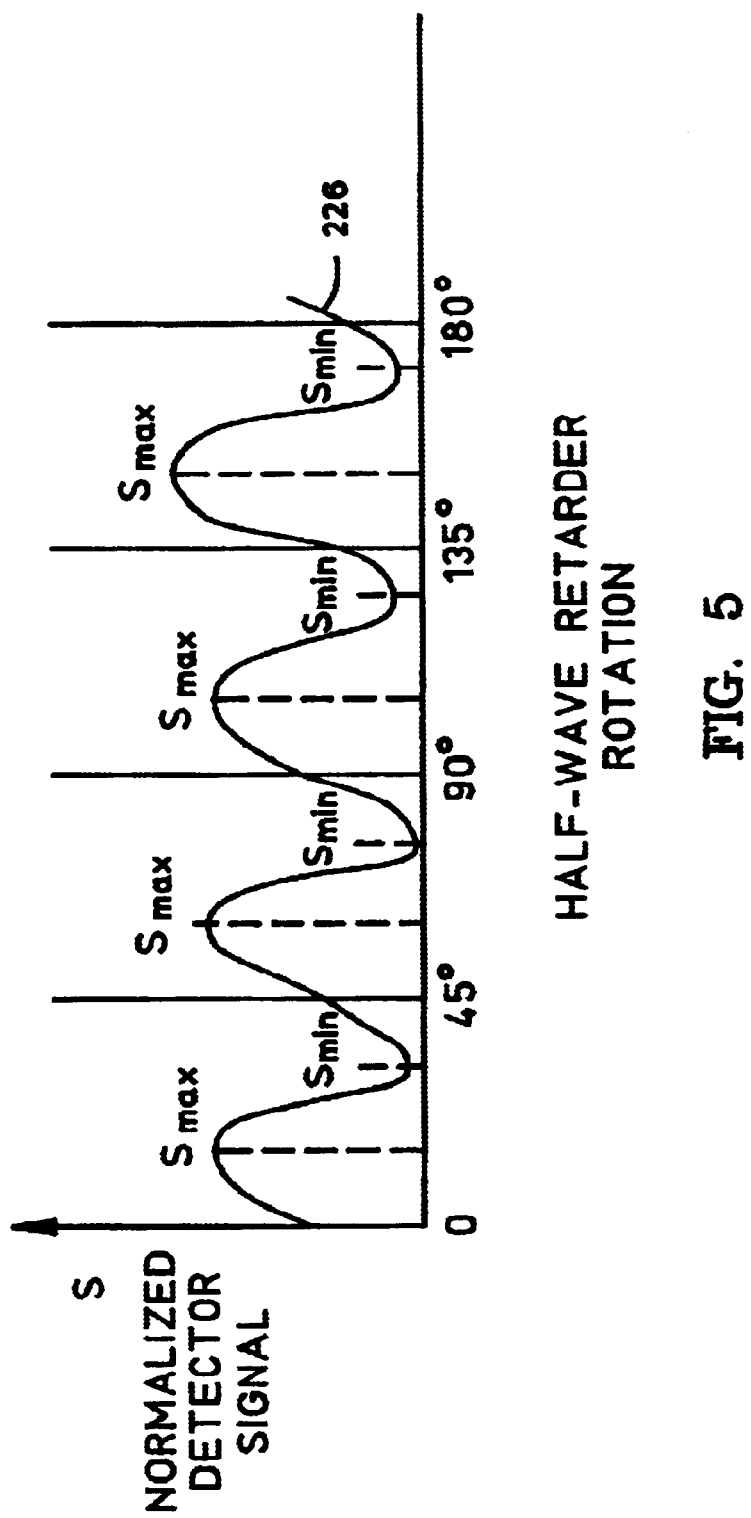
FIG. 5 is a chart illustrating the signal outputs from the optical polarization detector portion of the apparatus of FIG. 2.

As shown in FIG. 5, according to the method of this invention, a plurality magnitude extrema $\{S_{max}, S_{min}\}$ are obtained from of electrical signals 222 and 224 during the rotation over a one-hundred-and-eighty (180) degree range of half-wave plate portion of rotator 194. These extrema $\{S_{max}, S_{min}\}$ are then averaged by some suitable processor (such as, for example, averager 149 in FIG. 3) to produce the mean signal extrema $[\overline{S}_{max}, \overline{S}_{min}]$, which may then be used to determine the unbiased polarization state of reflected diagnostic signal 208, where $\theta = \text{Arc } \sin \sqrt{\overline{S}_{max} - \overline{S}_{min}}$. This procedure cancels any polarization bias arising from system birefringence (residual birefringence in the optical system) including the birefringence of rotator 194, as has been demonstrated by the inventors using a computer-implemented model of the polarimeter system 228 illustrated in FIG. 6.

Figure 6:
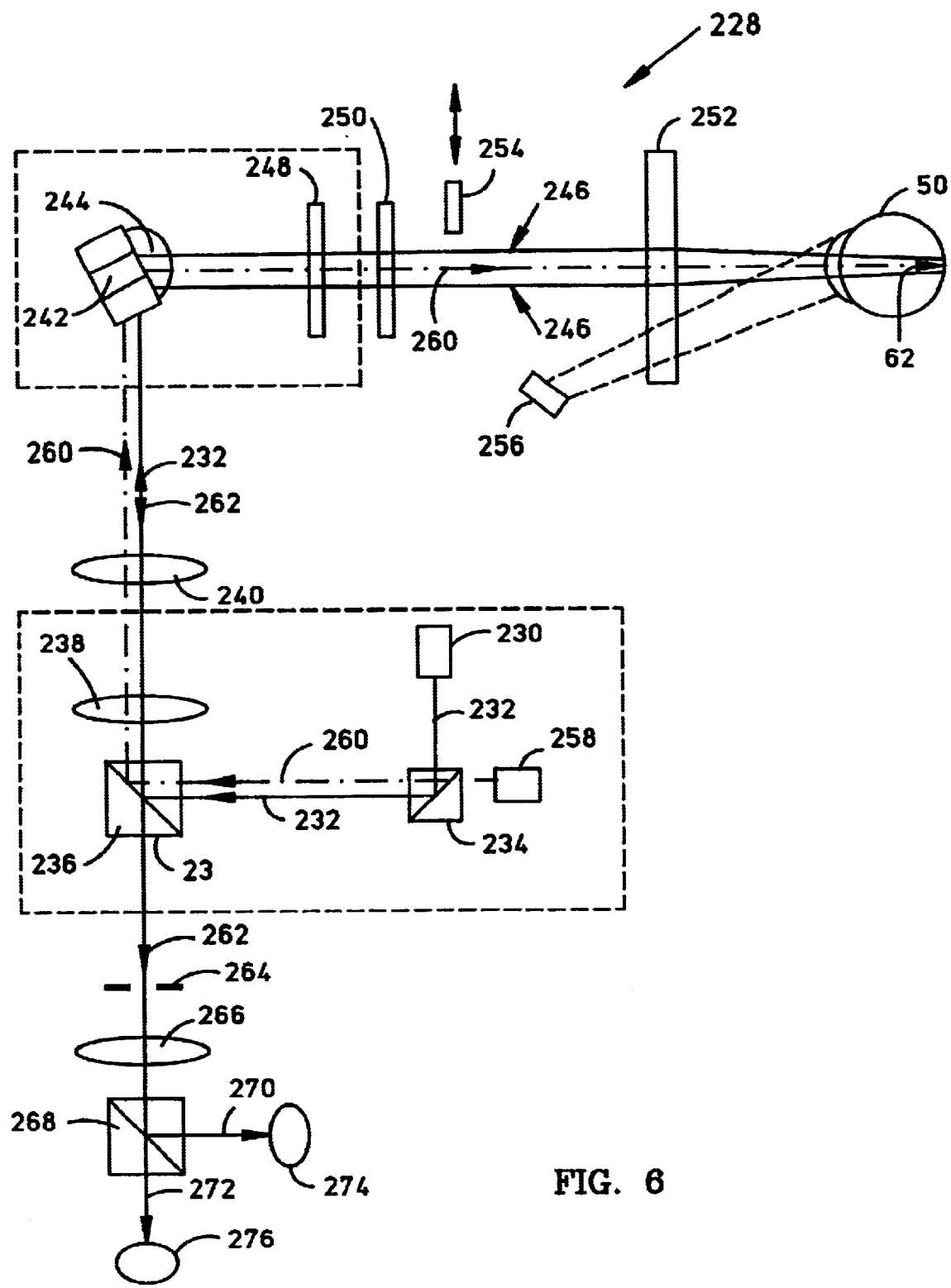
FIG. 6 is a functional block diagram illustrating yet another exemplary embodiment of a polarimeter apparatus for use in the opthalmological apparatus of this invention.

FIG. 6 is a functional block diagram illustrating yet another exemplary embodiment 228 of the polarimeter portion of the opthalmological apparatus of this invention. In FIG. 6, a laser diode 230 produces a linearly-polarized diagnostic optical signal 232, which is redirected by the polarizing beam splitter 234 to a non-polarizing beam splitter 236 and therefrom though the collimating lense 238 and the focusing lens 240 along an optical bean axis to the polygon scanner 242 and the galvo-mirror scanner 244. Scanners 242 and 244 provide a two-dimensional beam scan 246, each individual pixel of which has a linear polarization that is rotated by the half-wave plate 248 and the fixed retarder 250. An output lense 252 steers the elements of two-dimensional beam scan 246 to the fundus 62 of eye 50. A moveable calibration test target 254 is used in cooperation with a CCD camera 256 and a fixation laser diode 258 (providing an optical fixation signal 260 that is transmitted along the optical beam axis) to automatically calibrate and orient the various elements of polarimeter system 228 to eye 50. A reflected optical diagnostic signal 262 is returned from fundus 62 along the same optical path, to non-polarizing beam splitter 236, from whence it is transmitted through the pinhole 264 and the focusing lens 266 to the polarizing beam splitter 268. Polarizing beam splitter 268 separates the orthogonal polarization components 270 and 272, directing them respectively to the optical detectors 274 and 276. Operation of polarimeter system 228 may be readily appreciated with reference to the above discussions of FIGS. 1–5. Not shown is the motor means required for rotating half-wave plate about optical beam axis 260 to obtain the signal extrema data required in accordance with this invention.

The inventors have confirmed through computer modeling studies that the method of this invention cancels all system birefringence in the optical elements of polarimeter system 228. For a nominal 390 nm wave-plate providing a nominal 180 degrees of retardance using a diagnostic optical signal with a wavelength of 785 nm (a 2.5 nm mismatch between wave-plate and signal wavelength) and a Stokes vector of [1,–1,0,0], the following extrema were computed for a 60.57 nm test target oriented at four different angles with respect to the diagnostic optical signal, which provides 27.78 degrees of unbiased retardance. The retardance values are computed using the relationship, $\theta = \text{Arc } \sin \sqrt{\overline{S}_{max} - \overline{S}_{min}}$.

| 180° range | First 45° range | Second 45° range | Third 45° range | Fourth 45° range | $[\overline{S}_{max}, \overline{S}_{min}]$ |
|---|---|---|---|---|---|
| First Target Orientation | | | | | |
| $S_{max}$ | 0.228994 | 0.20566 | 0.20566 | 0.228994 | 0.217327 |
| $S_{min}$ | 0.000313 | 0 | 0.000313 | 0 | 0.000157 |
| $S_{max}-S_{min}$ | 0.228681 | 0.20566 | 0.205347 | 0.228994 | 0.217171 |
| Retardance | 28.67° | 26.97° | 26.95° | 28.59° | 27.78° |
| Error | 0.89° | –0.81° | –0.83° | 0.81° | –0.00° |
| Second Target Orientation | | | | | |
| $S_{max}$ | 0.233939 | 0.217214 | 0.200943 | 0.217214 | 0.217328 |
| $S_{min}$ | 0.000156 | 0.000156 | 0.000158 | 0.000158 | 0.000157 |
| $S_{max}-S_{min}$ | 0.233783 | 0.217058 | 0.200785 | 0.217056 | 0.217171 |
| Retardance | 28.91° | 27.77° | 26.62° | 27.77° | 27.78° |
| Error | 1.13° | –0.01° | –1.16° | –0.01° | –0.00° |

-continued

| 180° range | First 45° range | Second 45° range | Third 45° range | Fourth 45° range | $[\overline{S}_{max}, \overline{S}_{min}]$ |
|---|---|---|---|---|---|
| Third Target Orientation | | | | | |
| $S_{max}$ | 0.20566 | 0.228994 | 0.228994 | 0.20566 | 0.217327 |
| $S_{min}$ | 0.000313 | 0 | 0.000313 | 0 | 0.000157 |
| $S_{max}-S_{min}$ | 0.205347 | 0.228994 | 0.228681 | 0.20566 | 0.217171 |
| Retardance | 26.95° | 28.59° | 28.57° | 26.97° | 27.78° |
| Error | −0.83° | 0.81° | 0.79° | −0.81° | −0.00° |
| Fourth Target Orientation | | | | | |
| $S_{max}$ | 0.200943 | 0.217214 | 0.233939 | 0.217214 | 0.217328 |
| $S_{min}$ | 0.000158 | 0.000158 | 0.000156 | 0.000156 | 0.000157 |
| $S_{max}-S_{min}$ | 0.200785 | 0.217056 | 0.233783 | 0.217058 | 0.217171 |
| Retardance | 26.62° | 27.77° | 28.91° | 27.77° | 27.78° |
| Error | −1.16° | −0.01° | 1.13° | −0.01° | −0.00° |

Figure 7:
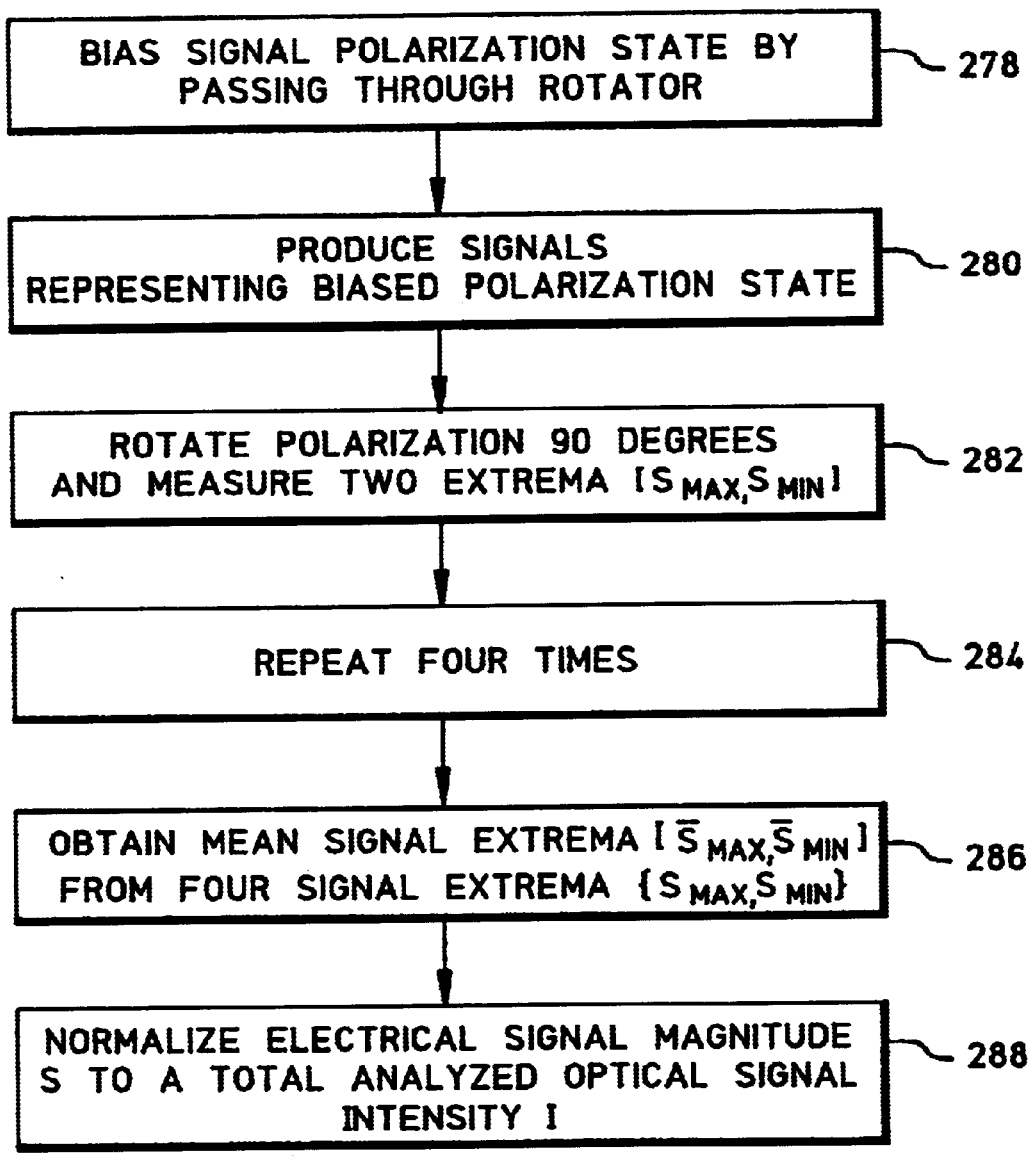
FIG. 7 is a block diagram of a flow chart illustrating an exemplary embodiment of the method of this invention.

FIG. 7 is a block diagram of a flow chart illustrating an exemplary embodiment of the method of this invention. At the first step 278, an analyzed optical signal is rotated by passing through a polarization rotator. In step 280, electrical signals are produced representing the biased polarization state of the analyzed optical signal. The analyzed optical signal polarization is rotated by 90-degrees about the beam axis in step 282 and the electrical signal extrema are noted; this step is repeated for a total of four times over a contiguous 360-degree range of rotation in step 284. The electrical signal extrema values are averaged in step 286 and normalized in step 288 as appropriate. The unbiased polarization state of the analyzed optical signal may then be computed from the averaged extrema values in the manner dictated by the particular polarimetry method employed. If a half-wave plate is employed to rotate analyzed optical signal polarization, the half-wave plate is rotated only over a 180-degree range to obtain the requisite four pairs of electrical signal extrema.

Figure 8:
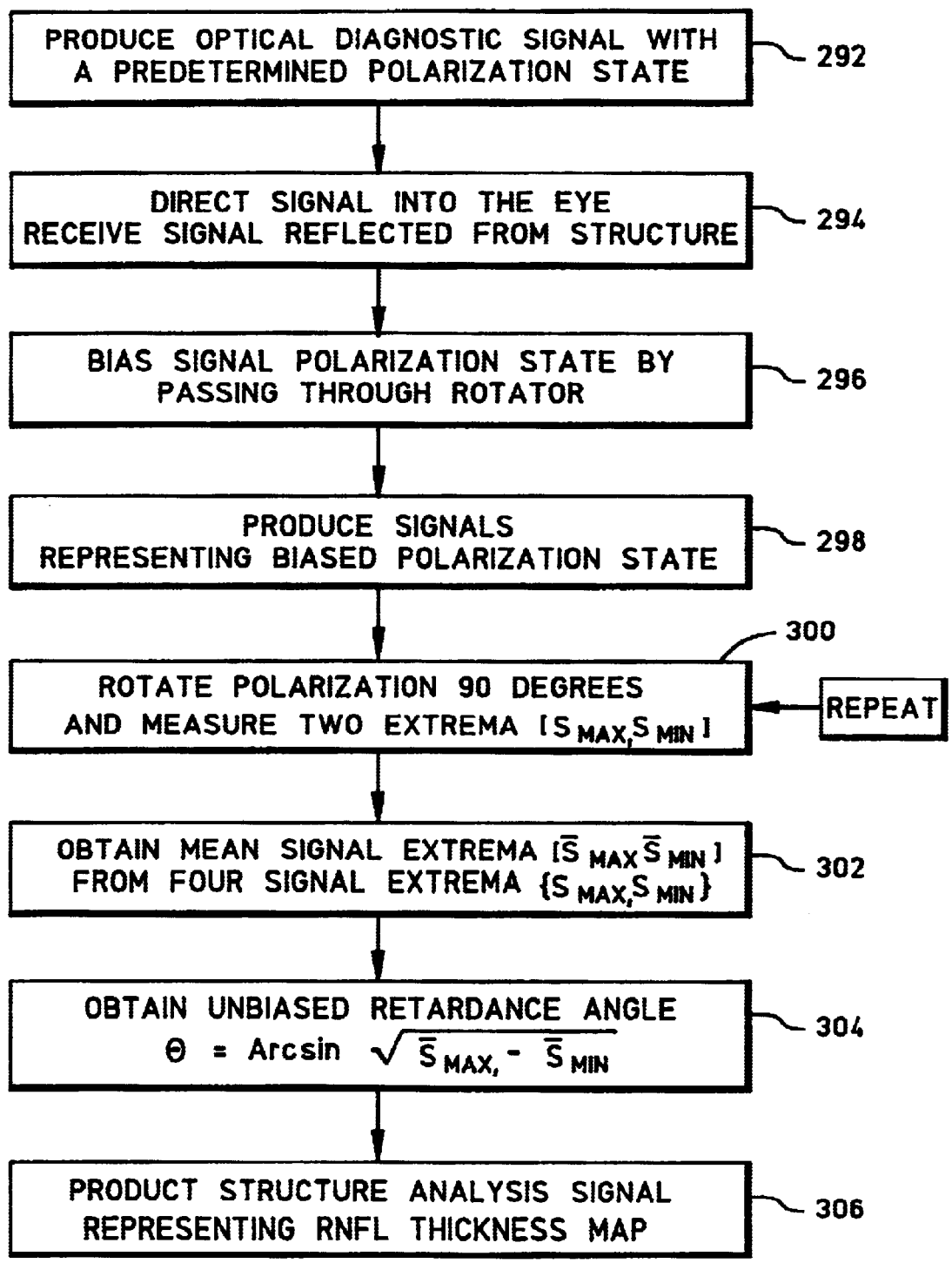
FIG. 8 is a block diagram of a flow chart illustrating an alternative embodiment of the method of this invention.

Similarly, FIG. 8 is a block diagram of a flow chart illustrating an alternative embodiment of the method of this invention. In the first step 292, an optical diagnostic signal is produced having a predetermined linear polarization state. This signal is directed into the eye and reflected from a structure in the eye in step 294. In step 296, the reflected diagnostic signal is biased by a polarization rotator and electrical signals representing the orthogonal polarization components of the biased reflected signal are produced in step 298. In Step 300, the reflected optical diagnostic signal polarization is rotated about the optical beam axis over a 90-degree range and two electrical signal extrema are measured. Step 300 is repeated four times and, in step 302, the mean electrical signal extrema are obtained. In step 304, the unbiased retardance of the reflected optical signal is calculated from the mean extrema and used to produce a RNFL thickness map in step 306. If a half-wave plate is employed to rotate reflected optical diagnostic signal polarization, the half-wave plate is rotated only over a 180-degree range to obtain the requisite four pairs of electrical signal extrema.

The method of this invention is particularly advantageous for ensuring accurate compensator retardance for canceling anterior segment retardance in an ophthalmological polarimeter. Laser wavelength may change because of temperature changes, thereby introducing errors even where the polarization rotator dimensions are otherwise perfect. Any error arising from residual system birefringence (bias) propagates into the RNFL (or other structure) measurements and cannot be eliminated at that stage of the process. The method of this invention is also particularly advantageous for accurately measuring both magnitude and axis of an unknown retardance when neither is known. Errors over the entire possible range of birefringence axis orientation are reduced. With a single-peak measurement, the retardance error may be minimized at some orientations and maximized at others. Because all orientations are found in human retinal structures, the error distribution over the structure is unpredictable without the method of this invention.

Clearly, other embodiments and modifications of this invention may occur readily to those of ordinary skill in the art in view of these teachings. Therefore, this invention is to be limited only by the, following claims, which include all such embodiments and modifications when viewed in conjunction with the above specification and accompanying drawing.

We claim:

1. A method for measuring the unbiased polarization state of an analyzed optical signal in an optical polarimeter system having a system birefringence, the method comprising the steps of:
   (a) producing an electrical signal having a magnitude S representing the polarization state of the analyzed optical signal as biased by the system birefringence;
   (b) rotating the analyzed optical, signal polarization about an optical beam axis over a substantially ninety (90) degree range within which the electrical signal magnitude S varies between two extrema $[S_{max}, S_{min}]$; and
   (c) averaging a plurality of electrical signal magnitude extrema $\{S_{max}, S_{min}\}$ obtained during rotation of the analyzed optical signal polarization over a substantially three-hundred-and-sixty (360) degree range to produce one or more mean electrical signal magnitude extrema signals $[\overline{S}_{max}, \overline{S}_{min}]$ representing the polarization state of the analyzed optical signal unbiased by the system birefringence.

2. The method of claim 1 further comprising the steps of:
   (b.1) passing the analyzed optical signal through a half-wave retarder along the optical beam axis;
   (b.2) rotating the half-wave retarder about the optical beam axis over a substantially forty-five (45) degree range within which the electrical signal magnitude S varies between two extrema $[S_{max}, S_{min}]$; and
   (c.1) averaging the plurality of electrical signal magnitude extrema $\{S_{max}, S_{min}\}$ obtained during rotation of the half-wave retarder over a substantially one-hundred-and-eighty (180) degree range to produce the mean electrical signal magnitude extrema signals $[\overline{S}_{max}, \overline{S}_{min}]$.

3. The method of claim 1 further comprising the step of:
   (a.1) normalizing the electrical signal magnitudes S to a total analyzed optical signal intensity I.

4. An optical polarimeter system for measuring the polarization state of an analyzed optical signal and having a system birefringence, the system comprising:
   input means for accepting the analyzed optical signal;
   optical polarization detector means for producing an electrical signal having a magnitude S representing the polarization state of the analyzed optical signal as biased by the system birefringence;
   polarization rotator means for rotating the analyzed optical signal polarization about an optical beam axis over a substantially ninety (90) degree range within which the electrical signal magnitude S varies between two extrema $[S_{max}, S_{min}]$; and processor means coupled to the optical polarization detector means for averaging a plurality of electrical signal magnitude extrema $\{S_{max}, S_{min}\}$ obtained during rotation of the analyzed optical signal polarization over a substantially three-hundred-and-sixty (360) degree range to produce one or more mean electrical signal magnitude extrema signals $[\overline{S}_{max}, \overline{S}_{min}]$ representing the polarization state of the analyzed optical signal unbiased by the system birefringence.

5. The system of claim 4 further comprising:
at least two optical polarization detectors for detecting at least two different polarization components of the analyzed optical signal.

6. The system of claim 4 further comprising:
a half-wave retarder and means for rotating the half-wave retarder about the optical beam axis over a substantially forty-five (45) degree range within which the electrical signal magnitude S varies between the two extrema $[S_{max}, S_{min}]$; and
means for averaging the plurality of electrical signal magnitude extrema $\{S_{max}, S_{min}\}$ obtained during rotation of the half-wave retarder over a substantially one-hundred-and-eighty (180) degree range to produce the mean electrical signal magnitude extrema signals $[\overline{S}_{max}, \overline{S}_{min}]$.

7. The system of claim 4 further comprising:
means for normalizing the electrical signal magnitude S to a total analyzed optical signal intensity I.

8. A method for analyzing a structure in the interior of an eye having a pupil, comprising the steps of:
(a) producing an optical diagnostic signal having a predetermined polarization state;
(b) directing the optical diagnostic signal into the eye through the pupil, such that the optical diagnostic signal is reflected from the structure back through the pupil;
(c) producing an electrical signal having a magnitude S representing the polarization state of the reflected optical diagnostic signal as biased by a system birefringence;
(d) rotating the reflected optical diagnostic signal polarization about an optical beam axis over a substantially ninety (90) degree range within which the electrical signal magnitude S varies between two extrema $[S_{max}, S_{min}]$;
(e) averaging a plurality of electrical signal magnitude extrema $\{S_{max}, S_{min}\}$ obtained during rotation of the reflected optical diagnostic signal polarization over a substantially three-hundred-and-sixty (360) degree range to produce one or more mean electrical signal magnitude extrema signals $[\overline{S}_{max}, \overline{S}_{min}]$ representing the polarization state of the reflected optical diagnostic signal unbiased by the system birefringence; and
(f) producing, responsive to the mean electrical signal magnitude extrema signals $[\overline{S}_{max}, \overline{S}_{min}]$, an analysis signal representative of a property of the structure.

9. The method of claim 8 further comprising the step of:
(e.1) producing a polarimetry signal representing the retardance $\theta = \text{Arc sin}\sqrt{\overline{S}_{max} - \overline{S}_{min}}$ of the structure.

10. The method of claim 8 further comprising the steps of:
(d.1) passing the reflected analyzed optical signal through a half-wave retarder along the optical beam axis;
(d.2) rotating the half-wave retarder about the optical beam axis over a substantially forty-five (45) degree range within which the electrical signal magnitude S varies between the two extrema $[S_{max}, S_{min}]$; and
(e.1) averaging the plurality of electrical signal magnitude extrema $\{S_{max}, S_{min}\}$ obtained during rotation of the half-wave retarder over a substantially one-hundred-and-eighty (180) degree range to produce the mean electrical signal magnitude extrema signals $[\overline{S}_{max}, \overline{S}_{min}]$.

11. The method of claim 8 further comprising the step of:
(d.1) normalizing the electrical signal magnitude S to a total analyzed optical signal intensity I.

12. The method of claim 8 wherein the structure includes a retinal nerve fiber layer (RNFL), further comprising the step of:
(g.1) producing a signal representative of a retardance of the RNFL.

13. The method of claim 8 further comprising the step of:
(g.1) producing an image signal representing an image of one or more retardance characteristics of the structure.

14. An apparatus for analyzing a structure in the interior of an eye having a pupil, the apparatus having a system birefringence and comprising:
optical source means for producing an optical diagnostic signal having a predetermined polarization state;
optics system means coupled to the optical source means for directing the optical diagnostic signal into the eye through the pupil, such that the optical diagnostic signal is reflected from the structure back through the pupil to the optics system means;
optical polarization detector means for producing an electrical signal having a magnitude S representing the polarization state of the reflected optical diagnostic signal as biased by a system birefringence;
polarization rotator means for rotating the reflected optical diagnostic signal polarization about an optical beam axis over a substantially ninety (90) degree range within which the electrical signal magnitude S varies between two extrema $[S_{max}, S_{min}]$; and
processor means coupled to the optical polarization detector means for producing, responsive to the polarization state of the reflected optical diagnostic signal, an image signal representative of a property of the structure, including
averager means for averaging a plurality of electrical signal magnitude extrema $\{S_{max}, S_{min}\}$ obtained during rotation of the reflected optical diagnostic signal polarization over a substantially three-hundred-and-sixty (360) degree range to produce one or more mean electrical signal magnitude extrema signals $[\overline{S}_{max}, \overline{S}_{min}]$ representing the polarization state of the reflected optical diagnostic signal unbiased by the system birefringence.

15. The apparatus of claim 14 further comprising:
at least two optical polarization detectors for detecting at least two different polarization components of the reflected optical diagnostic signal.

16. The apparatus of claim 14 further comprising:
means for producing a polarimetry signal representing the unbiased retardance $\theta = \text{Arc sin}\sqrt{\overline{S}_{max} - \overline{S}_{min}}$ of the structure.

17. The apparatus of claim 14 further comprising:
a half-wave retarder and means for rotating the half-wave retarder about the optical beam axis over a substantially forty-five (45) degree range within which the electrical signal magnitude S varies between the two extrema $[S_{max}, S_{min}]$; and means for averaging the plurality of electrical signal magnitude extrema $\{S_{max}, S_{min}\}$ obtained during rotation of the half-wave retarder over a substantially one-hundred-and-eighty (180) degree range to produce the mean electrical signal magnitude extrema signals $[\overline{S}_{max}, \overline{S}_{min}]$.

18. The apparatus of claim 14 further comprising:

means for normalizing the electrical signal magnitude S to a total reflected optical diagnostic signal intensity I.

19. The apparatus of claim 14 wherein the structure includes a retinal nerve fiber layer (RNFL), further comprising:

means for producing a signal representative of a retardance of the RNFL.

20. The apparatus of claim 14 further comprising:

means for producing an image signal representing an image of one or more retardance characteristics of the structure.

* * * * *